United States Patent [19]

Reiner et al.

[11] Patent Number: 4,458,072
[45] Date of Patent: Jul. 3, 1984

[54] ACYL DERIVATIVES

[75] Inventors: Roland Reiner, Basel; URS Weiss, Pratteln, both of Switzerland

[73] Assignee: Hoffmann-La Roche Inc., Nutley, N.J.

[21] Appl. No.: 305,870

[22] Filed: Sep. 28, 1981

[51] Int. Cl.³ .................... C07D 51/56; A61K 31/545
[52] U.S. Cl. ........................................ 544/22; 544/25; 544/27; 544/28; 548/100; 424/246
[58] Field of Search ...................... 544/22, 25, 27, 28; 548/100

[56] References Cited

U.S. PATENT DOCUMENTS 4,200,575  4/1980  Numata ............................... 424/246
4,341,775  7/1982  Takaya ............................... 424/246

Primary Examiner—Robert Gerstl
Attorney, Agent, or Firm—Jon S. Saxe; Bernard S. Leon; Frank P. Hoffman

[57] ABSTRACT

There are presented compounds of the formula

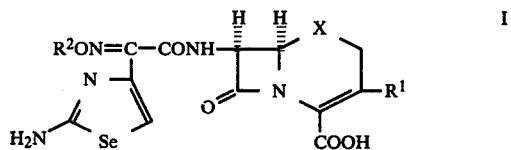

wherein $R^1$ is one of the 3-substituents usable in cephalosporin chemistry, $R^2$ is hydrogen, lower alkyl or $COOR^3$-lower alkyl, wherein $R^3$ is hydrogen, a cation of a base or a readily hydrolyzable ester group, and X is sulphur, oxygen or one of the groups —SO— and —SO$_2$—, and the readily hydrolyzable esters, readily hydrolyzable ethers and salts of these compounds and hydrates of the compounds of formula I or of their esters, ethers and salts, also presented are methods for the manufacture of these compounds as well as compounds used in their manufacture.

20 Claims, No Drawings

ACYL DERIVATIVES

Description of the Invention

The present invention relates to novel acyl derivatives, namely cephalosporin derivatives of the formula

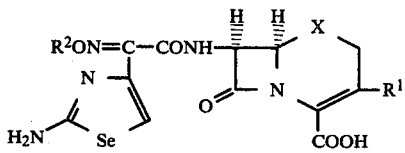

wherein $R^1$ is one of the 3-substituents usable in cephalosporin chemistry, $R^2$ is hydrogen, lower alkyl or $COOR^3$-lower alkyl, wherein $R^3$ is hydrogen, a cation of a base or a readily hydrolyzable ester group, and X is sulphur, oxygen or one of the groups —SO— and —SO$_2$—, and the readily hydrolyzable esters, readily hydrolyzable ethers and salts of these compounds and hydrates of the compounds of formula I or of their esters, ethers and salts.

The 3-substituent usable in cephalosporin chemistry can be a 3-substituent generally nown in cephalosporin chemistry, for example hydrogen, methyl, methoxy, chlorine or a group —CH$_2$Y in which Y signifies the residue of a nucleophilic compound. Examples of groups falling under the definition of Y are acetoxy, carbamoyloxy or groups of the general formula

in which $R^4$ represents hydrogen or carbamoyl; or a group —$SR^5$ in which $R^5$ represents an optionally substituted 5- or 6-membered hetrocycle with 1-4 hetero atoms (e.g. oxygen, sulphur, selenium and/or nitrogen). Examples of $R^5$ are tetrazolyl, triazolyl, thiadiazolyl and triazinyl. These groups can also be substituted, for example by lower alkyl such as methyl or ethyl, by halogen such as chlorine or bromine, by hydroxy or oxo groups. Examples of such substituted groups are the 1-methyl-tetrazol-5-yl,- 2-methyl-1,3,4-thiadiazol-5-yl, 1,4,5,6-tetrahydro-4-methyl-5,6-dioxo-as-triazin-3-yl, 2,5-dihydro-6-hydroxy-2-methyl-5-oxo-as-triazin-3-yl and 1,2,5,6-tetrahydro-2-methyl-5,6-dioxo-as-triazin-2-yl group.

In addition to hydrogen, $R^2$ can signify lower alkyl (e.g. $C_{1-4}$ alkyl such as methyl, ethyl, n-propyl, isopropyl or n-butyl) or also $COOR^3$-lower alkyl in which $R^3$ represents hydrogen, a cation of a base or a readily hydrolyzable ester group. These significances are illustrated in more detail hereinafter.

In the group "$COOR^3$-lower alkyl" the carboxy group can be situated on any position of the alkyl residue such as, for example, in 1-carboxyethyl, 2-carboxyethyl, 1-carboxy-1-methyl-ethyl, 2-carboxy-1-methyl-ethyl, 1-carboxy-1-methyl-n-propyl and carboxymethyl. 1-Carboxy-1-methyl-ethyl is preferred.

As readily hydrolyzable esters of the compounds of formula I there are to be understood compounds of formula I, the carboxy group(s) of which (i.e. the 3-carboxy group and/or the carboxy group of a carboxy-lower-alkyl group $R^2$) is/are present in the form of readily hydrolyzable ester groups. Examples of such esters, which can be of the conventional type, are the lower alkanoyloxyalkyl esters (e.g. the acetoxymethyl, pivaloyloxymethyl, 1-acetoxyethyl and 1-pivaloyloxyethyl ester), the lower alkoxycarbonyloxyalkyl esters (e.g. the methoxycarbonyloxymethyl, 1-ethoxycarbonyloxyethyl and 1-isopropoxycarbonyloxyethyl ester), the lactonyl esters (e.g. the phthalidyl and thiophthalidyl ester), the lower alkoxymethyl esters (e.g. the methoxymethyl ester) and the lower alkanoylaminomethyl esters (e.g. the acetamidomethyl ester). Other esters (e.g. the benzyl and cyanomethyl esters) can also be used.

As readily hydrolyzable ethers of the compounds of formula I there are to be understood compounds of formula I in which $R^1$ represents a group —$CH_2SR^5$ with a heterocycle $R^5$ substituted by a hydroxy group, the hydroxy group being present in the form of a readily hydrolyzable ether group. An example of such a hydroxy-substituted heterocycle $R^5$ is the 2,5-dihydro-6-hydroxy-2-methyl-5-oxo-as-triazin-3-yl group.

As ether groups there come into consideration the same groups as have already been mentioned above for the readily hydrolysable ester groups. Examples of such ethers are thus, for example, the lower alkanoyloxyalkyl ethers (e.g. the acetoxymethyl, pivaloyloxymethyl, 1-acetoxymethyl and 1-pivaloyloxyethyl ether), the lower alkoxycarbonyloxyalkyl ethers (e.g. the methoxycarbonyloxymethyl, 1-ethoxycarbonyloxyethyl and 1-isopropoxycarbonyloxyethyl ether), the lactonyl ethers (e.g. the phthalidyl and thiophthalidyl ether), the lower alkoxymethyl ethers (e.g. the methoxymethyl ether) and the lower alkanoylaminomethyl ethers (e.g. the acetamidomethyl ether).

Example of salts of the compounds of formula I are alkali metal salts such as the sodium and potassium salt, the ammonium salt, alkaline earth metal salts such as the calcium salt, salts with organic bases such as salts with amines (e.g. salts with N-ethyl-piperidine, procaine, dibenzylamine, N,N'-dibenzylethylenediamine, alkylamines or dialkylamines) as well as salts with amino acids such as, for example, salts with arginine or lysine. The salts can be mono-salts, di-salts or tri-salts. The further salt formations can occur in compounds with the hydroxy group of a hydroxy-substituted heterocycle $R^5$ or with the carboxy group of a carboxy-lower alkyl group $R^2$.

The compounds of formula I also form addition salts with organic or inorganic acids. Examples of such salts are hydrohalides (e.g. hydrochlorides, hydrobromides and hydroiodides) as well as other mineral acid salts such as sulphates, nitrates, phosphates and the like, alkylsulphonates and monoarylsulphonates such as ethanesulphonates, toluenesulphonates, benzenesulphonates and the like and also other organic acid salts such as acetates, tartrates, maleates, citrates, benzoates, salicylates, ascorbates and the like.

The compounds of formula I as well as their salts, readily hydrolyzable esters and ethers can be hydrated. The hydration can be effected in the course of the manufacturing process or can occur gradually as a result of hygroscopic properties of an initially anhydrous product.

The product in accordance with the invention can be present in the syn-isomeric form

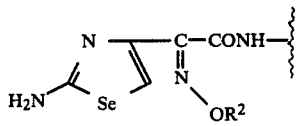

or in the anti-isomeric form

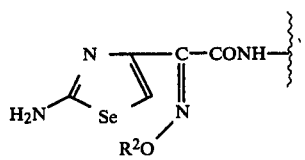

or as a mixture of these two forms. The syn-isomeric form or mixtures in which the syn-isomeric form predominates is/are preferred.

Preferred products are:
(6R,7R)-7-[2-(2-amino-4-selenazolyl)-2-[(Z)-methoxyimino]-acetamido]-3-[[(2,5-dihydro-6-hydroxy-2-methyl-5-oxo-as-triazin-3-yl)thio]-methyl]-8-oxo-5-thia-1-azabicyclo[4.2.0]oct-2-ene-2-carboxylic acid,
(6R,7R)-7-[2-(2-amino-4-selenazolyl)-2-[(Z)-methoxyimino]-acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid 5-oxide,
(6R,7R)-7-[2-(2-amino-4-selenazolyl)-2-[(Z)-methoxyimino]-acetamido]-3-methyl-8-oxo-5-thia-1-azabicyclo[4.2.0]oct-2-ene-2-carboxylic acid, methylene (6R,7R)-7-[2-(2-amino-4-selenazolyl)-2-[(Z)-methoxyimino]-acetamido]-3-methyl-8-oxo-5-thia-1-azabicyclo[4.2.0]oct-2-ene-2-carboxylate pivalate,
(6R,7R)-7-[2-(2-amino-3-selenazolyl)-2-[(Z)-methoxyimino]-acetamido]-3-[[(5-methyl-1,3,4-thiadiazol-2-yl)thio]methyl]-8-oxo-5-thia-1-azabicyclo[4.2.0]oct-2-ene-2-carboxylic acid,
(6R,7R)-7-[2-(2-amino-4-selenazolyl)-2-[(Z)-methoxyimino]-acetamido]-3-[[(1-methyl-1H-tetrazol-5-yl)thio]-methyl]-8-oxo-5-thia-1-azabicyclo[4.2.0]oct-2-ene-2-carboxylic acid,
(6R,7R)-7-[2-(2-amino-4-selenazolyl)-2-[(Z)-methoxyimino]-acetamido]-8-oxo-3-[[(1,4,5,6-tetrahydro-4-methyl-5,6-dioxo-as-triazin-3-yl)thio]methyl]-5-thia-1-azabicyclo[4.2.0]oct-2-ene-2-carboxylic acid,
(6R,7R)-3-(acetoxymethyl)-7-[2-(2-amino-4-selenazolyl)-2-[(Z)-methoxyimino]-acetamido]-8-oxo-5-thia-1-azabicyclo[4.2.0]oct-2-ene-2-carboxylic acid,
(6R,7R)-3-(acetoxymethyl)-7-[(Z)-2-(2-amino-4-selenazolyl)-2-[(1-carboxy-1-methylethoxy)imino]-acetamido]-8-oxo-5-thia-1-azabicyclo[4.2.0]oct-2-ene-2-carboxylic acid,
1-[[(6R,7R)-7-[(Z)-2-(2-amino-4-selenazolyl)-2-[(1-carboxy-1-methylethoxy)imino]-acetamido]-2-carboxy-8-oxo-5-thia-1-azabicyclo[4.2.0]oct-2-en-3-yl]methyl]pyridinium hydroxide (internal salt)
and their salts as well as corresponding hydrates.

The above acyl derivatives are manufactured in accordance with the invention by (a) reacting a compound of the formula

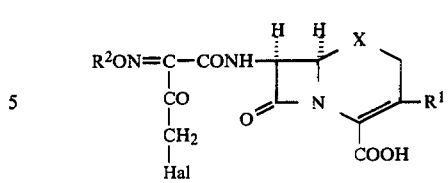

in which $R^1$, $R^2$ and X are as above, Hal is halogen and the carboxy group can be present in protected form, or a salt of this compound with selenourea and, if desired, cleaving off a carboxy protecting group which may be present, or (b) cleaving off the protecting group R and, if desired, a carboxy protecting group which may be present from a compound of the general formula

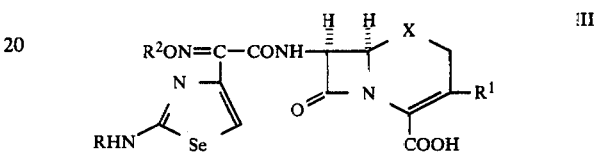

in which $R^1$, $R^2$ and X are as above, R is a cleavable protecting group and the carboxy group can be present in protected form, or from a salt of this compound, or (c) for the manufacture of compounds of formula I in which $R^1$ is the group $—CH_2SR^5$, wherein $R^5$ is as above, reacting a compound of the formula

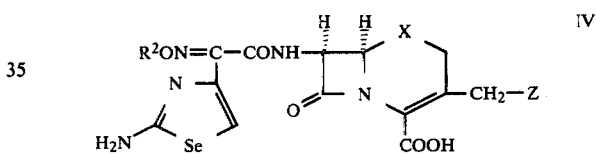

in which $R^2$ and X are as above, Z is a leaving group and the carboxy group can be protected by salt formation with an inorganic or tertiary organic base, or a salt of this compound in the presence of water with a thiol of the formula $$HS—R^5 \qquad V$$

in which $R^5$ is as above, and, if desired, cleaving off a carboxy protecting group which may be present, or (d) for the manufacture of compounds of formula I in which X represents one of the groups —SO— and —$SO_2$—, oxidizing a compound of formula I in which X represents sulfur or the group —SO— or a salt of this compound, or (e) for the manufacture of a readily hydrolyzable ester or ether of a compound of formula I, subjecting a carboxylic acid or an enol of formula I to a corresponding esterification, or (f) for the manufacture of salts or hydrates of a compound of formula I or hydrates of these salts, converting a compound of formula I into a salt or hydrate or into a hydrate of said salt.

If desired, the carboxy group present in the 3-position of the starting materials of formulae II and III can be protected; for example, by esterification to form a readily cleavable ester such as the silyl ester, e.g. the trimethylsilyl ester. The readily hydrolyzable esters mentioned above also come into consideration. The carboxy group can also be protected by salt formation with an inorganic or tertiary organic base such as triethylamine.

The reaction of a halide of formula II or a salt thereof with selenourea in accordance with variant (a) of the process in accordance with the invention is preferably carried out in an inert solvent such as, for example, a lower alkanol (e.g. ethanol), a lower ketone such as acetone, an ether such as tetrahydrofuran or dioxan, dimethylformamide, dimethylacetamide, water or in mixtures thereof. The reaction temperature generally lies in the range of about 0° C. to 60° C., preferably at room temperature. The chloride, bromide, fluoride or iodide can be used as the halide of formula II, the chloride or the bromide is preferably used. The free acid of formula II or, if desired, a salt thereof can be used, whereby the same salts as the salts of the compounds of formula I mentioned above come into consideration.

After carrying out process variant (a), a carboxy protecting group which may be present in the reaction product can be cleaved off if desired. When the protecting group is a silyl group (silyl ester), this group can be cleaved off especially readily by treating the reaction product with water. Lower alkanoyloxyalkyl, alkoxycarbonyloxyalkyl, lactonyl, alkoxymethyl and alkanoylaminomethyl esters are preferably cleaved enzymatically with the aid of a suitable esterase (at about 20°–40° C.). When the carboxy group is protected by salt formation (e.g. with triethylamine), then the cleavage of this salt-forming protecting group can be carried out by treatment with acid. The acid which can be used for this purpose can be, for example, hydrochloric acid, sulphuric acid, phosphoric acid or citric acid.

The protecting groups R in the starting materials of formula III used in variant (b) of the process in accordance with the invention are, for example, protecting groups which are cleavable by acid hydrolysis such as, for example, t-butoxycarbonyl or trityl, or protecting groups which are cleavable by basic hydrolysis such as, for example, trifluoroacetyl. Preferred R-protecting groups are chloroacetyl, bromoacetyl and iodoacetyl, especially chloroacetyl. The latter protecting groups can be cleaved off by treatment with thiourea.

The starting materials of formula III can be prepared, for example, by N-acylating the corresponding 7-amino compound, namely by reacting a compound of the formula

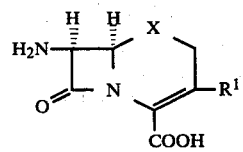

VI in which X and $R^1$ are as above and the carboxy group and/or the amino group can be present in protected form, with an acid of the formula

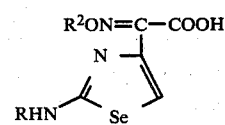

VII in which R and $R^2$ are as above, or with a reactive functional derivative of this acid and, if desired, cleaving off a carboxy protecting group possibly present.

If desired, the carboxy group present in the 7-amino compound of formula VI can be protected in the manner mentioned above for the starting materials of formulae II, III and IV to be prepared. The amino group of the compound of formula III can be protected, for example, by a silyl protecting group such as trimethylsilyl.

As reactive functional derivatives of acids of formula VII there come into consideration, for example, halides (i.e. chlorides, bromides and fluorides), azides, anhydrides, especially mixed anhydrides with strong acids, reactive esters (e.g. N-hydroxysuccinimide esters) and amides (e.g. imidazolides).

The reaction of the 7-amino compound of formula VI with the acid of formula VII or a reactive functional derivative thereof can be carried out in a manner known per se. Thus, for example, a free acid of formula VII can be condensed with one of the aforementioned esters corresponding to formula VI by means of a carbodiimide such as dicyclohexylcarbodiimide in an inert solvent such as ethyl acetate, acetonitrile, dioxan, chloroform, methylene chloride, benzene or dimethylformamide and subsequently the ester group can be cleaved off. Oxazolium salts (e.g. N-ethyl-5-phenyl-isoxazolium 3'-sulphonate) can also be used as the condensation agent in place of carbodiimides.

According to another embodiment, a salt of an acid of formula VI (e.g. a trialkylammonium salt such as the triethylammonium salt) is reacted with a reactive functional derivative of an acid of formula VII as mentioned above in an inert solvent (e.g. one of the solvents named above).

According to a further embodiment, an acid halide, preferably the chloride, of an acid of formula VII is reacted with the amine of formula VI. The reaction is preferably carried out in the presence of an acid-binding agent, for example, in the presence of aqueous alkali, preferably sodium hydroxide, or in the presence of an alkali metal carbonate such as potassium carbonate or in the presence of a lower-alkylated amine such as triethylamine. As the solvent there is preferably used water, optionally in admixture with an inert organic solvent such as tetrahydrofuran or dioxan. The reaction can also be carried out in an aprotic organic solvent such as, for example, dimethylformamide, dimethyl sulphoxide or hexamethylphosphoric acid triamide. When silylated starting materials of formula VI are used, the reaction is carried out in an anhydrous medium.

The reaction of the 7-amino compound of formula VI with the acid of formula VII or a reactive functional derivative thereof can conveniently be carried out at temperatures between about −40° C. and room temperature, for example at about 0°–10° C.

Starting materials of formula III in which $R^1$ is the group —$CH_2SR^5$ and R is not monohalogenated (as in bromoacetyl, chloroacetyl or iodoacetyl) can also be prepared by thiolation, namely by reacting a compound of the general formula

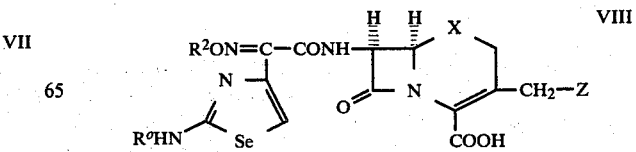

VIII in which X and $R^2$ are as above, $R^0$ is equal to R but can not be monohalogenated, Z is a leaving group and the carboxy group can be protected by salt formation with an inorganic or tertiary organic base, with a thiol of the general formula

HS—$R^5$    V in which $R^5$ is as above, and, if desired, cleaving off a carboxy protecting group which may be present.

As the leaving group Z in a compound of formula VIII there come into consideration, for example, halogens (e.g. chlorine, bromine or iodine), acyloxy groups (e.g. lower alkanoyloxy groups such as acetoxy), lower alkylsulphonyloxy or arylsulphonyloxy groups such as mesyloxy or tosyloxy, or the azido group.

The reaction of a compound of formula VIII with a thiol of formula V can be carried out in a manner known per se; for example, at a temperature between about 40° and 80° C., conveniently at about 60° C., in water or in a buffer solution with a pH of about 6 to 7, preferably 6.5. The carboxy group of the resulting compound of formula III can be protected if desired (e.g. by salt formation or esterification).

7-Amino compounds of formula VI in which $R^1$ represents the group —$CH_2SR^5$ can be prepared starting from a compound of the formula

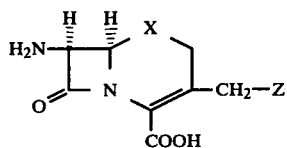    IX in which X is as above, Z is a leaving group and the carboxy group can be protected by salt formation with an inorganic or tertiary organic base, with a thiol of formula V in the presence of water. The reaction can be carried out under the same conditions as those which have been described for the reaction of the starting materials VIII with V. Alternatively, the compounds of formula VIII can be prepared starting from a compound of formula IX and an acid of formula VII or a reactive functional derivative thereof under the same conditions which have been described for the reaction of the compounds of formulae VI and VII.

The carboxy group and/or the amino group of the resulting compound of formula VI can be protected if desired, for example by subjecting the carboxy group to esterification or salt formation or by silylation.

The acids of formula VII can be prepared, for example, by reacting a compound of the formula

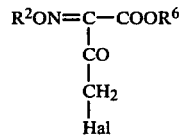    X in which $R^2$ and Hal are as above and $R^6$ is lower alkyl, especially methyl or ethyl, with selenourea in the same manner described above for the reaction of the starting materials of formula II with selenourea. The thus-obtained compound off the formula

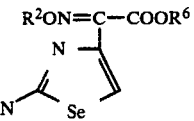    XI wherein $R^2$ and $R^6$ are as above, is subsequently protected at the amino group, preferably by reaction with the corresponding halide of the formula R-Hal, and the resulting compound of the formula

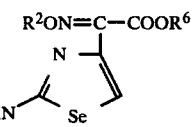    XII wherein R, $R^2$ and $R^6$ are as above, is subjected to acidic or alkaline saponification in order to cleave the ester group $R^6$. The reactive derivatives of the thus-obtained acids of formula VII are prepared in a manner known per se.

The thiols of formula V are in tautomeric equilibrium with the corresponding thiones. The ether group of thiols (thiones) which are etherified in the 6-position is generally introduced by reacting a S-protected thiol (e.g. by benzhydryl) with the halide containing the ether group, preferably the iodide, in an inert organic solvent in the presence of an acid-binding agent (e.g. potassium carbonate), preferably at about 10°–50° C., and cleaving off the protecting group (benzhydryl can be cleaved off with anisole and trifluoroacetic acid at room temperature).

In accordance with variant (b) of the process in accordance with the invention, the amino protecting group R of a starting material of formula III is cleaved off. Protecting groups which are cleavable by acid hydrolysis are preferably removed with the aid of a lower alkanecarboxylic acid which may be halogenated. In particular, formic acid or trifluoroacetic acid is used. This cleavage is generally carried out at room temperature, although it can also be carried out at a slightly higher or slightly lower temperature (e.g. a temperature in the range of about 0° C. to +40° C.). Protecting groups which are cleavable under alkaline conditions are generally hydrolyzed with dilute aqueous caustic alkali at 0° C. to 30° C. The chloroacetyl, bromoacetyl and iodoacetyl protecting groups can be cleaved off by means of thiourea in acidic, neutral or alkaline medium at about 0°–30° C. Hydrogenolytic cleavage (e.g. cleavage of benzyl) is unsuitable, since the oxime function is reduced to the amino group during the hydrogenolysis.

The carboxy protecting group which may be present can be cleaved off in the same manner as described above for process variant (a). The carboxy protecting group can also be cleaved off in the same manner prior to the cleavage of the protecting group R.

The starting materials of formula IV used in variant (c) of the process in accordance with the invention can be prepared by cleaving off the amino protecting group R from a compound of formula VIII above. This cleavage can be carried out in the same manner as the previously described cleavage of the amino protecting group R from a compound of formula III.

As the leaving group Z in a compound of formula IV there come into consideration, for example, halogens (e.g. chlorine, bromine or iodine), acyloxy groups (e.g. lower alkanoyloxy groups such as acetoxy), lower alkylsulphonyloxy or arylsulphonyloxy groups such as mesyloxy or tosyloxy or the azido group.

The reaction of a compound of formula IV with a thiol of formula V can be carried out in a manner known per se; for example at a temperature between about 40° and 80° C., conveniently at about 60° C., in water or in a buffer solution with a pH of about 6 to 7, preferably 6.5. The carboxy protecting group which may be present can be cleaved off in the same manner as described above for process variant (a).

Variant (d) of the process in accordance with the invention, namely the oxidation of compounds of formula I in which X represents sulphur or the group —SO— or a salt thereof, is carried out by treatment with an organic or inorganic oxidizing agent. As the oxidizing agent there can be used various compounds which readily yield oxygen such as, for example, organic peroxides, for example, monosubstituted organic peroxides such as $C_1$–$C_4$ alkyl or alkanoyl hydroperoxides (e.g. t-butyl hydroperoxide, performic acid and peracetic acid) as well as phenyl-substituted derivatives of these hydroperoxides such as cumene hydroperoxide and perbenzoic acid. The phenyl substituent can, if desired, carry a further lower group (e.g. $C_1$–$C_4$alkyl or alkoxy), halogen or a carboxy group (e.g. 4-methylperbenzoic acid, 4-methoxyperbenzoic acid, 3-chloroperbenzoic acid and monoperphthalic acid). As the oxidizing agent there can also be used various inorganic oxidizing agents, for example hydrogen peroxide, ozone, permanganates such as potassium or sodium permanganate, hypochlorites such as sodium, potassium or ammonium hypochlorite, peroxymonosulphuric acid and peroxydisulphuric acid. The use of 3-chloroperbenzoic acid is preferred. The oxidation is advantageously carried out in an inert solvent, for example in an aprotic inert solvent such as tetrahydrofuran, dioxan, methylene chloride, chloroform, ethyl acetate or acetone or in a protic solvent such as water, a lower alkanol (e.g. methanol or ethanol) or a lower alkanecarboxylic acid which may be halogenated (e.g. formic acid, acetic acid or trifluoroacetic acid). The oxidation is preferably carried out at a temperature in the range of −20° C. to +50° C.

When using equimolar amounts of oxidizing agent or a slight excess thereof in relation to the compound of formula I in which X represents sulphur or a salt thereof there is mainly obtained the corresponding sulphoxide of formula I in which X represents the group —SO—. If the amount of oxidizing agent is increased to double the stoichiometric ratio or more, the corresponding sulphone of formula I in which X represents the group —$SO_2$— is formed. It is likewise possible to obtain the sulphone of formula I from the corresponding sulphoxide by treatment with the oxidizing agent in equimolar or larger amount. The process conditions are essentially the same as in the manufacture of the sulphoxide.

In order to manufacture the readily hydrolyzable (mono or di) esters of the carboxylic acids of formula I in accordance with process variant (e), the carboxylic acid is preferably reacted with the corresponding halide containing the ester group, preferably with the iodide. The reaction can be accelerated with the aid of a base (e.g. an alkali metal hydroxide or carbonate or an organic amine such as triethylamine). When $R^1$ represents a group —$CH_2SR^5$ with a hydroxy-substituted heterocycle, the hydroxy groups are etherified with the formation of corresponding, readily hydrolyzable ethers. In this case an excess of the corresponding halide is preferably used. The esterification/etherification is preferably carried out in an inert organic solvent such as dimethylacetamide, hexamethylphosphoric acid triamide, dimethyl sulphoxide or, preferably, dimethylformamide. The temperature preferably lies in the range of about 0°–40° C.

The manufacture of the salts and hydrates of the compounds of formula I or the hydrates of these salts can be carried out in a manner known per se; for example, by reacting a carboxylic acid of formula I with an equivalent amount of the desired base, conveniently in a solvent such as water or in an organic solvent such as ethanol, methanol, acetone etc. When a second or third equivalent of base is used, salt formation is also effected on a possibly present hydroxy-substituted heterocycle in the 3-position or on the carboxy group of a carboxylower alkyl group, $R^2$, a di-salt or tri-salt resulting. The temperature at which the salt formation is carried out is not critical. It is generally carried out at room temperature, but it can also be carried out at a temperature slightly above or below room temperature (e.g. in the range of 0° C. to +50° C.).

The manufacture of the hydrates usually takes place automatically in the course of the manufacturing process or as a result of the hygroscopic properties of an initially anhydrous product. For the controlled manufacture of a hydrate, a completely or partially anhydrous product (carboxylic acid of formula I or ester, ether or salt thereof) can be exposed to a moist atmosphere (e.g. at about +10° C. to +40° C.).

A syn/anti mixture of a compound of formula I which may be obtained can be separated into the corresponding syn- and anti-forms in the usual manner, for example by recrystallization or by chromatographical methods using a suitable solvent or solvent mixture.

The compounds of formulae I and III as well as the corresponding readily hydrolyzable esters, readily hydrolyzable ethers and salts or the hydrates of these products have antibiotic, especially bactericidal, activity. They possess a broad spectrum of activity against gram-positive and gram-negative microorganisms, including β-lactamase-forming Staphylococci, Streptococci and various β-lactamase-forming gram-negative bacteria, such as, for example, *Pseudomonas aeruginosa, Escherichia coli, Serratia marcescens,* Proteus and Klebsiella species.

The compounds of formulae I and III as well as the corresponding readily hydrolyzable esters, readily hydrolyzable ethers and salts or the hydrates of these products can be used for the treatment and prophylaxis of infectious diseases. A dailly dosage of about 0.1 g to about 2 g comes into consideration for adults. The parenteral administration of the compounds in accordance with the invention is especially preferred.

In order to demonstrate the antimicrobial activity of the aforementioned products, the following representative members were tested:

Product A:
(6R,7R)-7-[2-(2-amino-4-selenazolyl)-2-[(Z)-methoxyimino]-acetamido]-3-[[(1-methyl-1H-tetrazol-5-yl)-thio]methyl]-8-oxo-5-thia-1-azabicyclo[4.2.0]oct-2-ene-2-carboxylic acid sodium salt.

Product B:
(6R,7R)-7-[2-)2-amino-4-selenazolyl)-2-[(Z)-methoxyimino]-acetamido]-3-[[(5-methyl-1,3,4-thiadiazol- 2-yl)thio]methyl]-8-oxo-5-thia-1-azabicyclo[4.2.-0]oct-2-ene-2-carboxylic acid sodium salt.

Product C:
(6R,7R)-7-[2-(2-amino-4-selenazolyl)-2-[(Z)-methoxyimino]-acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid desodium salt.

Product D:
(6R,7R)-3-(acetoxymethyl)-7-[2-(2-amino-4-selenazolyl)-2-[(Z)-methoxyimino]-acetamido]-8-oxo-5-thia-1-azabicyclo[4.2.0]oct-2-ene-2-carboxylic acid disodium salt.

Product E:
(6R,7R)-7-[2-(2-amino-4-selenazolyl)-2-[(Z)-methoxyimino]-acetamido]-3-[[(2,5-dihydro-6-hydroxy-2-methyl-5-oxo-as-triazin-3-yl)-thio]methyl]-8-oxo-5-thia-1-azabicyclo[4.2.0]oct-2-ene-2-carboxylic acid 5-oxide disodium salt.

Product F:
(6R,7R)-7-[2-(2-amino-4-selenazolyl)-2-[(Z)-methoxyimino]-acetamido]-3-methyl-3-oxo-5-thia-1-azabicyclo[4.2.0]oct-2-ene-2-carboxylic acid sodium salt.

Product G:
(6R,7R)-7-[2-(2-amino-4-selenazolyl)-2-[(Z)-methoxyimino)-acetamido]-8-oxo-3-[[(1,4,5,6-tetrahydro-4-methyl-5,6-dioxo-as-triazin-3-yl)thio]methyl]-5-thia-1-azabicyclo[4.2.0]oct-2-ene-2-carboxylic acid sodium salt.

Product H:
Methylene (6R,7R)-7-[2-(2-amino-4-selenazolyl)-2-[(Z)-methoxyimino]-acetamido]-3-methyl-8-oxo-5-thia-1-azabicyclo[4.2.0]oct-2-ene-2-carboxylate pivalate.

Product I:
(6R,7R)-3-(acetoxymethyl)-7-[(Z)-2-(2-amino-4-selenazolyl)-2-[(1-carboxy-1-methylmethoxy)imino]acetamide]-8-oxo-5-thia-1-azabicyclo[4.2.0]oct-2-ene-2-carboxylic acid disodium salt.

Product K:
1-[[[(6R,7R)-7-[(Z)-2-(2-amino-4-selenazolyl)-2-[(1-carboxy-1-methylethoxy)imino]acetamido]-2-carboxy-8-oxo-5-thia-1-azabicyclo[4.2.0]oct-2-en-3-yl]methyl]pyridinium hydroxide sodium salt (internal salt).

Product L:
(6R,7R)-3-(acetoxymethyl)-7-[2-(2-amino-4-selenazolyl)-2-[(Z)-hydroxyimino]-acetamido]-8-oxo-5-thia-1-azabicyclo[4.2.0]oct-2-ene-2-carboxylic acid sodium salt.

Product M:
(6R,7R)-7-[2-[2-amino-4-selenazolyl]-2-[(Z)-hydroxyimino]-acetamido]-3-methyl-8-oxo-5-thia-1-azabicyclo[4.2.0]oct-2-ene-2-carboxylic acid sodium salt.

| Pathogen | Activity in vitro: Minimum inhibitory concentration (μg/ml) | | | | | | | | | | |
|---|---|---|---|---|---|---|---|---|---|---|---|
| | A | B | C | D | E | F | G | I | K | L | M |
| *Escherichia coli* | | | | | | | | | | | |
| strain 1 | 0.1 | 0.2 | 0.1 | 0.1 | 0.1 | 0.8 | 0.05 | 1.6 | 0.4 | ≦0.025 | 0.8 |
| strain 2 | 0.025 | 0.006 | 0.05 | 0.025 | 0.025 | 0.05 | 0.012 | 0.2 | 0.1 | ≦0.025 | 0.4 |
| strain 3 | 0.4 | 0.8 | 0.8 | | 0.8 | 12.5 | 0.2 | 0.8 | 0.8 | 1.6 | 50 |
| strain 4 | 0.2 | 0.2 | 0.4 | | 0.05 | 100 | 0.2 | — | 25 | 6.3 | 200 |
| strain 5 | 0.4 | 0.4 | 0.2 | | 0.4 | 3.1 | 0.2 | 0.4 | 0.4 | 0.1 | 3.1 |
| *Proteus mirabilis* | | | | | | | | | | | |
| strain 1 | 0.10 | 0.19 | 0.012 | 0.025 | | | | | | | |
| strain 2 | 0.10 | 0.19 | 0.025 | 0.05 | | | | | | | |
| strain 3 | 0.8 | 0.2 | 1.6 | | 0.05 | 0.1 | 0.4 | 0.1 | 0.4 | ≦0.025 | 0.8 |
| strain 4 | 0.05 | 0.4 | 0.012 | | 0.4 | 0.8 | 0.025 | 0.1 | 0.1 | 0.05 | 6.3 |
| strain 5 | 0.05 | 0.4 | 0.012 | | 0.1 | 0.4 | 0.025 | 0.2 | 0.05 | 0.05 | 1.6 |
| *Proteus morganii* | 0.1 | 0.05 | 0.05 | 0.39 | 0.1 | 50 | 0.05 | 0.8 | 0.2 | 0.4 | 100 |
| *Proteus rettgeri* | 0.2 | 0.2 | 0.1 | | 0.05 | 0.1 | 0.05 | 0.1 | — | — | 0.2 |
| *Proteus inconstans* | 0.025 | 0.025 | 0.006 | | 0.025 | ≦0.025 | 0.006 | 0.012 | 0.05 | ≦0.025 | 0.05 |
| *Proteus vulgaris* | 0.78 | 0.78 | 1.6 | 0.78 | | | | | | | |
| *Klebsiella pseumoniae* | | | | | | | | | | | |
| strain 1 | 0.2 | 0.4 | 0.1 | 0.2 | 0.1 | 0.2 | 0.1 | 0.8 | 0.8 | ≦0.025 | 0.8 |
| strain 2 | 0.05 | 0.1 | 0.05 | 0.025 | 0.05 | 0.05 | 0.05 | 0.4 | 0.2 | ≦0.025 | 0.4 |
| strain 3 | 0.1 | 0.2 | 0.1 | | 0.1 | 0.05 | 0.05 | 0.8 | 0.8 | ≦0.025 | 0.4 |
| *Serratia marcescens* | | | | | | | | | | | |
| strain 1 | 0.4 | 0.8 | 0.4 | 0.8 | 0.8 | 3.1 | 0.2 | 1.6 | 0.8 | 0.8 | 25 |
| strain 2 | 0.8 | 1.6 | 1.6 | 0.8 | 0.8 | 6.3 | 0.4 | 3.1 | 0.8 | 1.6 | 100 |
| strain 3 | 0.1 | 0.2 | 0.1 | | 0.2 | 0.4 | 0.1 | 0.4 | 0.1 | 0.1 | 6.3 |
| *Enterobacter cloacae* | | | | | | | | | | | |
| strain 1 | >100 | >100 | >100 | >100 | 1.6 | >200 | >100 | >100 | >100 | 200 | >200 |
| strain 2 | 0.8 | 1.6 | 3.1 | 3.1 | 0.2 | 25 | 0.8 | 6.3 | 1.6 | 6.3 | >200 |
| strain 3 | 50 | 50 | >100 | | 1.6 | >200 | 50 | >100 | 100 | 25 | >200 |
| *Enterobacter aerogenes* | | | | | | | | | | | |
| strain 1 | 0.1 | 0.1 | 0.1 | | 0.1 | 0.2 | 0.1 | 0.4 | 0.4 | ≦0.025 | 0.4 |
| strain 2 | 0.1 | 0.1 | 0.1 | | 0.05 | 0.2 | 0.1 | 0.2 | 0.2 | 0.4 | 1.6 |
| *Citrobacter freundii* | | | | | | | | | | | |
| strain 1 | 1.6 | 1.6 | 12.5 | 6.3 | 0.1 | 200 | 1.6 | 100 | 12.5 | 3.1 | 100 |
| strain 2 | 0.05 | 0.2 | 0.1 | | 0.1 | 1.6 | 0.1 | 1.6 | 0.4 | 0.025 | 1.6 |
| *Pseudomonas aeruginosa* | | | | | | | | | | | |
| strain 1 | 25 | 50 | 3.1 | 12.5 | 100 | >200 | 50 | | | 50 | >400 |
| strain 2 | 25 | 25 | 6.3 | 12.5 | 100 | >200 | 50 | | | | |
| strain 3 | 6.3 | 6.3 | 1.6 | 3.1 | 50 | 200 | 25 | 1.6 | 1.6 | 12.5 | >400 |
| *Staphylococcus aureus* | | | | | | | | | | | |
| strain 1 | 0.8 | 0.8 | 3.1 | 0.8 | >12 | 50 | 0.4 | 50 | 12.5 | 0.2 | 3.1 |
| strain 2 | 1.6 | 1.6 | 6.3 | 3.1 | >12 | 100 | 1.6 | 100 | 50 | 0.4 | 6.3 |

-continued

| Pathogen | Activity in vitro: Minimum inhibitory concentration (μg/ml) | | | | | | | | | | |
|---|---|---|---|---|---|---|---|---|---|---|---|
| | A | B | C | D | E | F | G | I | K | L | M |
| strain 3 | 0.8 | 0.8 | 3.1 | | >12 | 50 | 0.8 | 50 | 12.5 | 0.4 | 3.1 |
| strain 4 | 0.8 | 1.6 | 6.3 | | >12 | 100 | 0.8 | 100 | 12.5 | 0.4 | 6.3 |
| *Staphylococcus epidermidis* | 0.8 | 0.8 | 3.1 | | >12 | 100 | 0.8 | 50 | 12.5 | 0.4 | 3.1 |
| *Streptococcus faecalis* | | | | | | | | | | | |
| strain 1 | 100 | 100 | >100 | | >12 | >200 | 25 | >100 | >100 | 25 | 200 |
| strain 2 | >100 | 100 | >100 | | >12 | >200 | 50 | >100 | >100 | 25 | >200 |
| *Streptococcus pyogenes* | | | | | | | | | | | |
| strain 1 | 0.025 | 0.025 | 0.05 | 0.05 | 3.1 | 3.1 | 0.05 | 0.2 | 0.4 | 0.05 | 1.6 |
| strain 2 | ≦0.012 | ≦0.012 | ≦0.012 | | 0.2 | 0.05 | — | 0.05 | 0.1 | ≦0.025 | 0.1 |
| *Streptococcus pneumoniae* | 0.025 | 0.025 | 0.05 | | 3.1 | 12.5 | 0.1 | 0.2 | 0.1 | 0.1 | 6.3 |
| *Streptococcus viridans* | 0.8 | 0.8 | 3.1 | | >12 | 12.5 | 0.8 | 6.3 | 3.1 | 0.8 | 25 |

Activity in vivo

Groups of 5 mice are infected intraperitoneally with an aqueous suspension of various pathogens. The test substance in physiological sodium chloride solution is administered subcutaneously twice, i.e. 1 hour and 3 hours after the infection. The number of surviving animals is determined on the 4th day. Various dosages are administered and that dosage at which 50% of the experimental animals survive ($CD_{50}$, mg/kg) is determined by interpolation.

| Pathogen | Activity in vivo: $CD_{50}$, mg/kg | | | | | | | | | | |
|---|---|---|---|---|---|---|---|---|---|---|---|
| | A | B | C | D | E | F | G | H | I | K | L | M |
| *Escherichia coli* | 0.006 | 0.006 | <0.003 | <0.01 | 0.017 | 0.06 | <0.003 | 0.11 | 0.067 | | | 1.0 |
| *Pseudomonas aeruginosa** | 39 | 134 | 14 | 35 | .75 | >200 | >200 | >100 | 23 | 1.1 | | |
| *Klebsiella pneumoniae* | | | 0.23 | | | | | 0.44 | | | | |
| *Neisseria meningitidis*** | | | <0.05 | | <0.1 | | | | | | | |
| *Haemophilus influenzae* | 1.5 | 0.27 | <0.05 | | 1.8 | 4 | 0.25 | | | | | |
| *Enterobacter cloacae* | 8.4 | >12 | 17 | | 0.06 | >25 | 9.2 | >50 | | | | |
| *Serratia marcescens* | | | | | | | | | | | | |
| strain 1 | 0.13 | 0.52 | 0.07 | 0.14 | 0.03 | 0.59 | 0.2 | | 1.8 | 0.11 | | 3.5 |
| strain 2 | | | | | | 5.1 | | | | | | >50 |
| *Staphylococcus aureus* | | | | | | | | >12 | | | | 2.7 |
| *Streptococcus pyogenes* | 0.05 | 0.05 | 0.04 | 0.05 | 0.13 | <0.05 | 0.02 | 0.13 | 2.7 | 0.28 | 0.08 | 0.23 |

*Administered subcutaneously three times: 1 hour, 3 hours and 5 hours after the infection.
**Administered subcutaneously twice: 1 hour and 4 hours after the infection.

| Test substance | Toxicity, $LD_{50}$, mg/kg | |
|---|---|---|
| | Mode of administration | |
| | s.c. | p.o. |
| A (end product of Example 6) | >4000 | >5000 |
| B (end product of Example 5) | >4000 | >5000 |
| C (end product of Example 1) | >4000 | >5000 |
| D (end product of Example 8) | >4000 | >5000 |
| E (end product of Example 2) | >4000 | >5000 |
| F (end product of Example 3) | >4000 | >5000 |
| G (end product of Example 7) | >4000 | >5000 |
| H (end product of Example 4) | | >5000 |

The products in accordance with the invention can be used as medicaments, for example in the form of pharmaceutical preparations which contain them in admixture with a pharmaceutical, organic or inorganic inert carrier material which is suitable for enteral or parenteral administration such as, for example, water, gelatin, gum arabic, lactose, starch, magnesium stearate, talc, vegetable oils, polyalkyleneglycols, Vaseline etc. The pharmaceutical preparations can be made up in solid form (e.g. as tablets, dragées, suppositories or capsules) or in liquid form (e.g. as solutions, suspensions or emulsions). If necessary, they can be sterilized and/or can contain adjuvants such as preserving, stabilizing, wetting or emulsifying agents, salts for varying the osmotic pressure, anaesthetics or buffers. They can also contain still other therapeutically valuable substances. The compounds of formula I and their salts or hydrates are preferably administered parenterally and for this purpose are preferably prepared as lyophilizates or dry powders for dilution with customary agents such as water or isotonic sodium chloride solution. The readily hydrolyzable esters or ethers of the compounds of formula I and their salts or hydrates also come into consideration for enteral (e.g. oral) administration.

The following Examples illustrate the present invention:

EXAMPLE 1

Manufacture of the disodium salt of (6R,7R)-7-[2-(2-amino-4-selenazolyl)-2-[(Z)-methoxyimino]-acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid:

11.55 g of (6R,7R)-7-[4-bromo-2-[(Z)-methoxyimino]-3-oxobutyramido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid are dissolved in 160 ml of ethanol and treated at 25° C. with 2.7 g of selenourea. The mixture is stirred for 1½ hours at 25° C. while gassing with nitrogen and excluding light, resinous material firstly separating and then crystallization occurring. The crystallized-out hydrobromide is filtered off under suction, washed with ethanol and low-boiling petroleum ether and dried in vacuo at 40° C. There is obtained the reddish hydrobromide of the title substance which for conversion into the disodium salt, is firstly dissolved together with 4.5 g of sodium acetate trihydrate in a mixture of 35 ml of water and 35 ml of acetone. 35 ml of acetone are added to this solution until it becomes turbid. A small amount of insoluble, reddish selenium is filtered off by means of a fluted filter. A further 15 ml of acetone are added to the orange-yellow filtrate. The oily-resinous material which thereby separates is separated by means of a fluted filter and discarded. The crystallization of the disodium salt from the yellow filtrate is induced by rubbing with a glass rod. The mixture is left to crystallize for 1 hour and subsequently a further 50 ml of acetone are added dropwise to the crystallization mixture while stirring during about 1 hour until the crystallization is complete. The crystallizate is filtered off under suction, washed with 50 ml of acetone/water (85:15), acetone and low-boiling petroleum either and dried overnight in vacuo at 25° C. There is obtained light beige, voluminous title substance with $[\alpha]_D^{25} = -139°$ (c=0.5 in water). The nuclear resonance spectrum and the microanalysis correspond to the given structure. The substance contains 3.5 mol of water of crystallization.

The (6R,7R)-7-[4-bromo-2-[(Z)-methoxyimino]-3-oxobutyramido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid used as the starting material can be prepared as follows: 592.1 g of acetoacetic acid tert.butyl ester are dissolved in 560 ml of glacial acetic acid. To this solution is added dropwise at 5°–10° C. during 2½ hours a solution of 290.6 g of sodium nitrite in 655 ml of water. The resulting yellow suspension is stirred for 30 minutes at 20° C., treated with 940 ml of water and stirred for a further 2 hours. The mixture is treated with 900 ml of water and 900 g of ice and extracted in the stirring vessel three times with 1 l of ethyl acetate each time. The combined ethyl acetate extracts are washed three times with 1 l of water each time, then treated with 5 l of water and the pH-value is adjusted to 6.8 with sodium hydrogen carbonate. After separating the aqueous phase, the organic phase is washed once with water. Thereafter, the ethyl acetate solution is dried over sodium sulphate and evaporated in vacuo at 40° C. There is obtained (Z)-2-hydroxyimino-3-oxo-butyric acid tert-butyl ester as a yellow oil which is dried for a further 9 hours in a high vacuum at 40° C.

626.65 g of (Z)-2-hydroxyimino-3-oxo-butyric acid tert.butyl ester are dissolved in 2.86 l of acetone. The solution is cooled to 5° C. and treated portionwise with 703.5 g of potassium carbonate. 322 ml of dimethyl sulphate are then added dropwise to the yellow suspension without cooling during 1 hour, whereby the temperature of the mixture should not rise above 25° C. The light beige suspension is stirred at 20°–25° C. for about 4 hours until starting material can no longer be detected by thin-layer chromatography. Thereafter, the mixture is poured into 7 l of water and extracted three times with 1 l of ethyl acetate each time. The combined ethyl acetate extracts are washed three times with 1 l of water each time, dried over sodium sulphate and evaporated in vacuo at 40° C. The residual yellow oil is dried for a further 6 hours in a high vacuum at 40° C. and subsequently distilled. There is obtained (Z)-2methoxyimino-3-oxo-butyric acid tert.butyl ester as a yellow oil with a boiling point of 57° C. at 0.02 mmHg.

86 g of (Z)-2-methoxyimino-3-oxo-butyric acid tert.-butyl ester are dissolved in 400 ml of trifluoroacetic acid. The solution is left to stand for 1 hour at 25° C. and thereafter evaporated in vacuo at 35° C. The oily residue is crystallized from ether/petroleum ether. There is obtained yellowish, water-soluble (Z)-2-methoxyimino-3-oxo-butyric acid of melting point 80°–85° C.

145 g of (Z)-2-methoxyimino-3-oxo-butyric acid are dissolved in 1000 ml of alcohol-free anhydrous dichloromethane. 10 ml of 30% hydrobromic acid in glacial acetic acid are added to this solution. Then, a solution of 37.5 ml of bromine in 112.5 ml of dichloromethane are added dropwise during about 2 hours, the temperature of the mixture being held at 20°–25° C. by means of slight cooling. Now, in order to remove hydrogen bromide from the mixture, nitrogen is vigorously blown through. Subsequently, 250 g of ice, 250 ml of water and 2 l of ether are successively added. The aqueous phase is separated and discarded. The organic phase is washed with 250 ml of water and 250 ml of saturated sodium chloride solution, dried with sodium sulphate and evaporated in vacuo. There remains a brown oil which is crystallized from carbon tetrachloride. There is obtained almost colourless (Z)-4-bromo-2-methoxyimino-3-oxo-butyric acid.

37.1 g of (7R)-3-amino-3-desacetoxy-3-[(2,5-dihydro-6-hydroxy-2-methyl-5-oxo-as-triazin-3-yl)thio]cephalosporanic acid are suspended in 800 ml of ethyl acetate and treated with 100 ml of N,O-bis-(trimethylsilyl)-acetamide. The mixture is stirred while excluding moisture for 30 minutes at 25° C., a light yellow solution resulting. To this solution, cooled to −10° C., is added dropwise during 30 minutes at −10° to 0° C. a solution of (Z)-4-bromo-2-methoxyimino-3-oxo-butyric acid chloride, prepared from 22.4 g of (Z)-4-bromo-2-methoxyimino-3-oxo-butyric acid in 300 ml of alcohol-free anhydrous dichloromethane and 20.8 g of phosphorus pentachloride at 8°–10° C. The mixture is stirred for 30 minutes at 0.5° C. and for 1 hour at 25° C. 1 l of ethyl acetate and 500 ml of water are added thereto while stirring. The aqueous phase and the resinous intermediate layer are discarded. The organic phase is washed six times with 500 ml of water each time, dried with sodium sulphate and concentrated to a volume of 200 ml in vacuo at 40° C. This orange coloured concentrate is added dropwise while stirring to 1.8 l of ether, the product precipitating in amorphous form. This precipitate is filtered off under suction, washed successively with 1 l of ether and 1 l of low-boiling petroleum ether and dried overnight in vacuo at 35° C. There is obtained (6R,7R)-7-[4-bromo-2-[(Z)-methoxyimino]-3-oxobutyramido]-3-[[(2,5-dihydro-6-hydroxy-2-methyl-5-as-triazin-3-yl)thio]methyl]-8-oxo-5-thia-1-azabicyclo[4.2.0]-oct-2-ene-2-carboxylic acid as a beige, amorphous product with $[\alpha]_D^{25} = -223.1°$ (c=1 in methanol).

EXAMPLE 2

Manufacture of the disodium salt of (6R,7R)-7-[2-(2-amino-4-selenazolyl)-2-[(Z)-methoxyimino]-acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid 5-oxide:

5.93 g of (6R,7R)-7-[4-bromo-2-[(Z)-methoxyimino] -3-oxobutyramido]-3-[[(2,5-dihydro-6-hydroxy-2-methyl-5-oxo-as-triazin-3-yl)thio]methyl]-8-oxo-5thia-1-azabicyclo[4.2.0]oct-2-ene-2-carboxylic acid 5-oxide are suspended in a mixture of 30 ml of water and 30 ml of acetone and treated with 4.5 g of sodium acetate trihydrate as well as 1.35 g of selenourea. The mixture is stirred for 30 minutes at 25° C. Some insoluble, reddish material is separated by means of a fluted filter. The orange-yellow filtrate is treated with 15 ml of acetone until it becomes turbid, the product crystallizing immediately. The mixture is stirred for a further 15 minutes and then the crystallizate is filtered off under suction, washed with 50 ml of acetone/water (85:15), acetone and low-boiling petroleum ether and dried in vacuo at 25° C. There is obtained beige, crude title substance which, for recrystallization, is firstly dissolved in 30 ml of water. A small amount of insoluble selenium is removed by means of a fluted filter. The filtrate is treated with acetone until it becomes turbid, the disodium salt crystallizing out immediately. The mixture is stirred for a further 15 minutes. The disodium salt is filtered off under suction, washed with 50 ml of acetone/water (85:15), acetone and low-boiling petroleum ether and dried overnight in a high vacuum at 40°–45° C. Thereafter, the substance is brought to a constant water content by equilibration for 1 hour in the air. There is obtained light beige pure crystalline title substance with $[\alpha]_D^{25} = -117.5°$ (c=0.8 in water). The nuclear resonance spectrum and the microanalysis correspond to the given structure. The substance contains 6 mol of water.

The (6R,7R)-7-[4-bromo-2-[(Z)-methoxyimino]-3-oxobutyramido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid 5-oxide used as the starting material can be prepared as follows:

17.31 g of (6R,7R)-7-[4-bromo-2-[(Z)-methoxyimino]-3-oxobutyramido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid are dissolved in 170 ml of ethanol and treated portionwise during 45 minutes with 6.1 g of 3-chloroperbenzoic acid (85%). The product precipitates; the reaction is slightly exothermic; a temperature increase from 25° C. to 30° C. is observed. After the oxidizing agent has been added, the mixture is stirred for a further 15 minutes at about 25° C. The substance is filtered off under suction, washed with a small amount of ethanol, ether and low-boiling petroleum ether and dried in vacuo at 40° C. There is thus obtained a Fraction I of the desired product. The mother liquor is concentrated strongly in vacuo at 40° C. The material which thereby crystallizes out is filtered off under suction, washed with a small amount of ethanol, ether and low-boiling petroleum ether and dried in vacuo at 40° C. There is thus obtained a Fraction II of the desired product. For purification, the combined fractions I and II are firstly dissolved in 100 ml of methanol. This solution is diluted with 900 ml of ethanol. A small amount of insoluble material is filtered off and the yellow filtrate is concentrated strongly in vacuo at 40° C. The precipitated substance is filtered off under suction and washed with a small amount of ethanol, ether and low-boiling petroleum ether. There is obtained beige title substance with $[\alpha]_D^{25} = -244°$ (c=0.9 in methanol). For the recrystallization and preparation of high-purity material, 10 g of the thus-obtained substance are dissolved in 50 ml of acetone. The substance immediately again crystallizes out from this solution. It is filtered off under suction, washed with acetone and low-boiling petroleum ether and dried overnight in a high vacuum at 40°–45° C. There is obtained beige pure substance with $[\alpha]_D^{25} = -249.2°$ (c=1 in methanol). The nuclear resonance spectrum and the microanalysis correspond to the given structure.

EXAMPLE 3

Manufacture of the sodium salt of (6R,7R)-7-[2-(2-amino-4-selenazolyl)-2-[(Z)-methoxyimino]-acetamido]-3-methyl-8-oxo-5-thia-1-azabicyclo[4.2.0]oct-2-ene-2-carboxylic acid:

8.4 g of (6R,7R)-7-[4-bromo-2-[(Z)-methoxyimino]-3-oxobutyramido]-3-methyl-8-oxo-5-thia-1-azabicyclo[4.2.0]oct-2-ene-2-carboxylic acid are suspended in 160 ml of ethanol and treated with 2.7 g of selenourea. The mixture is stirred for 1 hour at 25° C. while gassing with nitrogen and excluding of light. The resulting solution is filtered through a fluted filter in order to separate a small amount of insoluble selenium. The yellow filtrate is treated with 22 ml of a 2 N solution of sodium 2-ethylcaproate in ethyl acetate, the pink coloured cephalosporin sodium salt precipitating. After adding 160 ml of methanol, there again results an orange solution which is filtered through a fluted filter in order to remove a small amount of finely divided, red selenium. The yellow filtrate is treated with 160 ml of ethanol and concentrated to a volume of about 100 ml in vacuo at 40° C. The material which thereby crystallizes out is filtered off under suction and washed with ethanol and low-boiling petroleum ether. There is obtained a Fraction I of the title substance. The mother liquor and the ethanol washings are concentrated further, substance again crystallizing out. This substance is filtered off under suction and washed with ethanol and low-boiling petroleum ether. There is obtained a Fraction II of the title substance. For purifications, the combined Fractions I and II are firstly dissolved in 100 ml of methanol. This solution is diluted with 400 ml of ethanol, a small amount of finely divided red selenium is filtered off by means of a fluted filter and the filtrate is concentrated strongly in vacuo at 40° C. The material which thereby crystallizes out is filtered off under suction, washed with ethanol and low-boiling petroleum ether and dried overnight in a high vacuum at 40°–45° C. There is obtained beige pure substance with $[\alpha]_D^{25} = +87°$ (c=1 in water). The nuclear resonance spectrum and the microanalysis correspond to the given structure.

The (6R,7R)-7-[4-bromo-2-[(Z)-methoxyimino]-3-oxobutyramido]-3-methyl-8-oxo-5-thia-1-azabicyclo[4.2.0]-oct-2-ene-2-carboxylic acid used as the starting material can be prepared as follows:

(a) Silylation of 7-aminodesacetoxycephalosporanic acid:

6.7 g of 7-aminodesacetoxycephalosporanic acid are suspended in 400 ml of ethyl acetate and treated with 50 ml of N,O-bis-(trimethylsilyl)-acetamide. The mixture is stirred for about 45 minutes at 35°–40° C. while excluding moisture, a pale yellow solution resulting. This solution is cooled to −10° to 15° C. and stored while excluding moisture until it is used in the acylation.

(b) Preparation of (Z)-4-bromo-2-methoxyimino-3-oxobutyric acid chloride:

11.2 g of (Z)-4-bromo-2-methoxyimino-3-oxo-butyric acid are treated in 150 ml of methylene chloride at 0°–5° C. with 10.4 g of phosphorus pentachloride. This solution is stirred for 15 minutes at 0°–5° C. and subsequently for 45 minutes without cooling.

(c) Acylation and working-up:

The acid chloride solution prepared according to (b) is added dropwise during about 30 minutes at −10° C. to the silylated 7-aminodesacetoxycephalosporanic acid described under (a). The mixture is stirred for 30 minutes at −10° to 0° C. and for about 1½ hours at 25° C. Thereafter, it is poured into a mixture of 500 ml of water and 1000 ml of ethyl acetate. The organic phase is washed four times with 500 ml of water each time, dried with sodium sulphate and concentrated strongly in vacuo at 40° C., the product crystallizing. This product is filtered off under suction, washed with ethyl acetate, ether and low-boiling petroleum ether and dried overnight in vacuo at 40° C. There is obtained pure white, statically-charged, crystalline pure substance with $[\alpha]_D^{25} = +86.8°$ (c=1 in dimethylformamide). The nuclear resonance spectrum corresponds to the given structure.

EXAMPLE 4

Manufacture of methylene (6R,7R)-7-[2-(2-amino-4-selenazolyl)-2-[(Z)-methoxyimino]acetamido]-3-methyl-8-oxo-5-thia-1-azabicyclo[4.2.0]oct-2-ene-2-carboxylate pivalate:

2.33 g of the sodium salt of (6R,7R)-7-[2-(2-amino-4-selenazolyl)-2-[(Z)-methoxyimino]-acetamido]-3-methyl-3-oxo-5-thia-1-azabicyclo[4.2.0]oct-2-ene-2-carboxylic acid are dissolved in 25 ml of dimethylformamide. This solution is cooled to 0°–5° C. and treated while gassing with nitrogen with 2.24 g of pivaloyloxymethyl iodide. The mixture is stirred for 30 minutes at 0°–5° C. and then poured into 500 ml of water. The aqueous phase is extracted twice with 250 ml of ethyl acetate each time. The combined organic phases are washed twice with 100 ml of water, twice with 100 ml of 5% sodium hydrogen carbonate solution and once more with 100 ml of water, dried over sodium sulphate and concentrated strongly in vacuo at 40° C. The product precipitates in amorphous form upon adding low-boiling petroleum ether. This product is filtered off under suction and washed with low-boiling petroleum ether. There is obtained a yellowish, amorphous crude product. For purifications, this crude product is chromatographed on a silica gel column using ethyl acetate as the eluting agent. The fractions containing the title compound are combined and evaporated in vacuo at 40° C. After reprecipitation from ethyl acetate/low-boiling petroleum ether, there is finally obtained light beige amorphous pure substance with $[\alpha]_D^{25} = +64.8°$ (c=1.07 in ethyl acetate). The nuclear resonance spectrum and the microanalysis correspond to the given structure.

EXAMPLE 5

Manufacture of the sodium salt of (6R,7R)-7-[2-(2-amino-4-selenazolyl)-2-[(Z)-methoxyimino]-acetamido]-3-[[(5-methyl-1,3,4-thiadiazol-2-yl)thio]methyl]-8-oxo-5-thia-1-azabicyclo[4.2.0]oct-2-ene-2-carboxylic acid:

5.5 g of (6R,7R)-7-[4-bromo-2-[(Z)-methoxyimino]-3-oxobutyramido]-3-[[(5-methyl-1,3,4-thiadiazol-2-yl)thio]methyl]-8-oxo-5-thia-1-azabicyclo[4.2.0]oct-2-ene-2-carboxylic acid are dissolved in 80 ml of ethanol and treated with 1.35 g of selenourea. The mixture is stirred for 1½ hours at 25° C. while gassing with nitrogen and excluding light. Resinous material separates out. After adding 300 ml of methanol, there are added to the resulting solution 11 ml of a 2 N solution of sodium 2-ethylcaproate salt in ethyl acetate. A small amount of brown sludge-like material is filtered off. The yellowish-brown filtrate is stirred with decolorizing carbon for 30 minutes at 25° C. and filtered. The light yellow filtrate is diluted with 500 ml of ethanol and concentrated strongly in vacuo at 40° C., the substance crystallizing out. The substance is filtered off under suction, washed with ethanol and low-boiling petroleum ether and dried overnight in a high vacuum at 40° C. There is obtained beige pure substance with $[\alpha]_D^{25} = -53.4°$ (c=1 in water). The nuclear resonance spectrum and the microanalysis correspond to the given structure.

The (6R,7R)-7-[4-bromo-2-[(Z)-methoxyimino]-3-oxobutyramido]-3-[[(5-methyl-1,3,4-thiadiazol-2-yl)thio]methyl]-8-oxo-5-thia-1-azabicyclo[4.2.0]oct-2-ene-2-carboxylic acid used as the starting material is prepared analogously to Example 1 and is obtained as a beige amorphous acid with the nuclear resonance spectrum corresponding to its structure.

EXAMPLE 6

Manufacture of the sodium salt of (6R,7R)-7-[2-(2-amino-4-selenazolyl)-2-[(Z)-methoxyimino]-acetamido]-3-[[(1-methyl-1H-tetrazol-5-yl)thio]methyl]-8-oxo-5-thia-1-azabicyclo[4.2.0]oct-2-ene-2-carboxylic acid:

10.7 g of (6R,7R)-7-[4-bromo-2-[(Z)-methoxyimino]-3-oxobutyramido]-3-[[(1-methyl-1H-tetrazol-5-yl)thio]methyl]-8-oxo-5-thia-1-azabicyclo[4.2.0]oct-2-ene-2-carboxylic acid are dissoled in 160 ml of ethanol and treated at 25° C. with 2.7 g of selenourea. The mixture is stirred for 1 hour at 25° C. while gassing with nitrogen and excluding light, resinous material separating out. After adding 200 ml of methanol, there results a solution to which are added 22 ml of a 2N solution of sodium 2-ethylcaproate in ethyl acetate. Thereby, the desired compound partially precipitates. A further 200 ml of methanol are added and the mixture is filtered off from a small amount of insoluble red selenium. The filtrate is treated with 200 ml of ethanol until it is slightly turbid and concentrated in vacuo at 40° C. After 200 ml of distillate have passed over, precipitated material is filtered off under suction and washed with ethanol and low-boiling petroleum ether. There is obtained a Fraction I which is discarded. The mother liquor is concentrated further in vacuo at 40° C. After a further 250 ml of distillate have passed over, precipitated material is filtered off under suction, washed with ethanol and low-boiling petroleum ether and dried overnight in a high vacuum at 45° C. There is obtained beige Fraction II with $[\alpha]_D^{20} = -22.1°$ (c=1 in water) which is the title substance. The nuclear resonance spectrum and the microanalysis correspond to the given structure.

The (6R,7R)-7-[4-bromo-2-[(Z)-methoxyimino]-3-oxobutyramido]-3-[[(1-methyl-1H-tetrazol-5-yl)thio]methyl]-8-oxo-5-thia-1-azabicyclo[4.2.0]oct-2-ene-2-carboxylic acid used as the starting mwaterial is prepared analogously to Example 1 and is obtained as a beige amorphous acid with $[\alpha]_D^{25} = -27.3$ (c=1 in methanol) with the nuclear resonance spectrum corresponding) to its structure.

EXAMPLE 7

Manufacture of the sodium salt of (6R,7R)-7-[2-(2--amino-4-selenazolyl)-2-[(Z)-methoxyimino]-acetamido]-8-oxo-3-[[(1,4,5,6-tetrahydro-4-methyl-5,6-dioxo-as-triazin-3-yl)thio]methyl]-5-thia-1-azabicyclo[4.2.0]oct-2-ene-2-carboxylic acid:

8.66 g of (6R,7R)-7-[4-bromo-2-[(Z)-methoxyimino]-3-oxobutyramido]-8-oxo-3-[[(1,4,5,6-tetrahydro-4-methyl-5,6-dioxo-as-triazin-3-yl)thio]methyl]-5-thia-1-azabicyclo[4.2.0]oct-2-ene-2-carboxylic acid are suspended in 120 ml of ethanol and treated with 2.03 g of selenourea. After stirring for about 10 minutes a thick suspension is still present. Consequently, 120 ml of methanol are added, whereby there partially results a solution from which, however, material again separates out. The mixture is evaporated in vacuo at 40° C. The reddish residue is dissolved in 300 ml of methanol and a small amount of insoluble selenium is filtered off. The filtrate is treated with 20 ml of a 2N solution of sodium 2-ethylcaproate in ethyl acetate, the cephalosporin sodium salt precipitating. Now, the mixture is diluted to 1 l with methanol and a small amount of insoluble material is filtered off. The yellow filtrate is treated with 250 ml of ethanol and concentrated strongly in vacuo at 40° C. The material which thereby precipitates is filtered off under suction, washed with ethanol and low-boiling petroleum ether and dried in vacuo at 40° C. There is obtained beige crude product which, for purification, is dissolved in 500 ml of methanol and treated with 250 ml of ethanol. The turbid solution is filtered through a fluted filter and the pale yellow filtrate is concentrated strongly in vacuo at 40° C. The precipitated material is filtered off udner suction and dried overnight at 40° C. in a high vacuum. There is obtained beige pure substance with $[\alpha]_D^{25} = -37.6°$ (c=1 in water). The nuclear resonance spectrum and the microanalysis correspond to the given structure.

The (6R,7R)-7-[4-bromo-2-[(Z)-methoxyimino]-3-oxobutyramido]-8-oxo-3-[[(1,4,5,6-tetrahydro-4-methyl-5,6-dioxo-as-triazin-3-yl)thio]methyl]-5-thia-1-azabicyclo[4.2.0]oct-2-ene-2-carboxylic acid used as the starting material is prepared analogously to Example 1 and is obtained as a beige crystalline acid with $[\alpha]_D^{25} = -141.7°$ (c=0.9% in dimethylformamide) with the nuclear resonance spectrum corresponding to its structure.

Example 8

Manufacture of the sodium salt of (6R,7R)-3-(acetoxymethyl)-7-[2-(2-amino-4-selenazolyl)-2-[(Z)-methoxyimino]acetamido]-8-oxo-5-thia-1-azabicyclo[4.2.0]oct-2-ene-2-carboxylic acid:

4.8 g of (6R,7R)-3-(acetoxymethyl)-7-[4-bromo-2-[(Z)-methoxyimino]-3-oxobutyramido]-8-oxo-5-thia-1-azabicyclo[4.2.0]oct-2-ene-2-carboxylic acid are dissolved in 25 ml of methanol and treated with 1.35 g of selenourea. The mixture is stirred for 1 hour at 25° C. while gassing with nitrogen and exclusing light. Then there are added 10 ml of a 2N solution of sodium 2-ethylcaproate in ethyl acetate. A small amount of insoluble red selenium is filtered off by means of a fluted filter. The yellow filtrate is diluted with about 150 ml of ethanol until it is slightly turbid. After filtration by means of a fluted filter, the yellow filtrate is concentrated strongly in vacuo at 40° C., the cephalosporin sodium salt crystallizing. This salt is filtered off under suction, washed with ethanol and low-boiling petroleum ether and dried overnight in a high vacuum at 40° C. There is obtained beige pure substance with $[\alpha]_D^{25} = +53.4°$ (c=1 in water). The nuclear resonance spectrum and the microanalysis correspond to the given structure.

The (6R,7R)-3-(acetoxymethyl)-7-[4-bromo-2-[(Z)-methoxyimino]-3-oxobutyramido]-8-oxo-5-thia-1-azabicyclo[4.2.0]oct-2-ene-2-carboxylic acid used as the starting material is prepared analogously to Example 1 and is obtained as a beige crystalline acid with $[\alpha]_D^{25} = +59.1°$ (c=1 in methanol) with the nuclear resonance spectrum and microanalysis corresponding to its structure.

Example 9

Manufacture of the disodium salt of (6R,7R)-3-(-acetoxymethyl)-7-[(Z)-2-(2-amino-4-selenazolyl)-2-[(1-carboxy-1-methylethoxy)imino]acetamido]-8-oxo-5-thia-1-azabicyclo[4.2.0]oct-2-ene-2-carboxylic acid:

39 g of (6R,7R)-3-(acetoxymethyl)-7-[2-[(Z)-[1-tert.-butoxycarbonyl)-1-methylethoxy]imino]-2-[2-(tritylamino)-4-selenazolyl]acetamido]-8-oxo-5-thia-1-azabicyclo[4.2.0]oct-2-ene-2-carboxylic acid tert.butyl ester are stirred in 400 ml of trifluoroacetic acid for 30 minutes at 25° C. The solution is evaporated in vacuo at 40° C. The residual resin is treated with low-boiling petroleum ether. The resulting solid is filtered off under suction, washed with low-boiling petroleum ether and dried overnight in vacuo at 40° C. There is obtained an amorphous, yellowish mixture which contains material still not completely cleaved. In order to complete the cleavage of the protective groups, the isolated material is dissolved in a mixture of 160 ml of trifluoroacetic acid and 160 ml of 100% formic acid and stirred for 1½ hours at 25° C. The solution is evaporated in vacuo at 40° C. The residue is stirred up with 500 ml of ether, filtered under suction, the filter material is washed with ether and low-boiling petroleum ether and dried in vacuo at 40° C. There is obtained the yellowish trifluoroacetate of the title substance. For conversion into the disodium salt, the trifluoroacetate is firstly dissolved in 500 ml of methanol. This solution is treated with 70 ml of a 2N solution of sodium 2-ethylcaproate in ethyl acetate and with 500 ml of ethanol. A small amount of precipitated material is filtered off and discarded. The orange coloured filtrate is concentrated strongly in vacuo at 40° C. The substance which thereby crystallizes out is filtered off under suction, washed with ethanol and low boiling petroleum ether and dried for 2 days in a high vacuum at 40° C. There is obtained yellowish title substance with $[\alpha]_D^{25} = +36.5°$ (c=1 in water). The nuclear resonance spectrum and the microanalysis correspond to the given structure.

The (6R,7R)-3-(acetoxymethyl)-7-[2-[(Z)-[1-tert.-butoxycarbonyl)-1-methylethoxy]imino]-2-[2-(tritylamino)-4-selenazolyl]acetamido]-8-oxo-5-thia-1-azabicyclo[4.2.0]oct-2-ene-2-carboxylic acid tert.butyl ester used as the starting material can be prepared as follows:

(a) Preparation of 2-amino-4-selenazolylacetic acid ethyl ester (Z)-oxime:

46.13 g of selenourea are dissolved in a mixture of 726 ml of ethanol and 363 ml of water. While gassing with nitrogen and cooling slightly at 20°-25° C. this solution is treated portionwise during about 15 minutes with 72.6 g of 4-chloro-2-(Z)-hydroxyimino-2-oxo-butyric acid ethyl ester. The solution is stirred for 1½ hours at 20°-25° C. while gassing with nitrogen and thereafter a small amount of separated, red selenium is filtered off. The light yellow filtrate is treated at 25° C. with a solution of 68 g of sodium acetate trihydrate in 726 ml of water, the pH rising from 2.8 to 5.3 and the product crystallizing out. The mixture is stirred for a further 1½ hours at 25° C. The product is filtered off under suction, washed with 250 ml of ethanol and low-boiling petroleum ether and dried overnight in vacuo at 45° C. There is obtained pure title substance of melting point 193°-195° C. (decomposition). The nuclear resonance spectrum and the microanalysis correspond to the given structure.

(b) Preparation of 2-tritylamino-4-selenazolylpyruvic acid ethyl ester (Z)-oxime hydrochloride:

72.1 g of 2-amino-4-selenazolylacetic acid ethyl ester (Z)-oxime are dissolved in 150 ml of dimethylformamide. The solution is filtered in order to separate traces of selenium. The yellow filtrate is treated with 38.25 ml of triethylamine, cooled to $-30°$ C. and treated while stirring during about 1½ hours with 76.25 g of trityl chloride at $-30°$ C. The temperature of the mixture is allowed to rise to 20°–25° C. during about 1 hour and then the mixture is stirred at 25° C. for a further 3 hours. The mixture is poured into 1 l of ethyl acetate and washed twice with 1 l of water each time. The brownish organic phase obtained in treated with 1 l of 1N aqueous hydrochloric acid and shaken well, the hydrochloride precipitating. This hydrochloride is filtered off under suction, washed successively with a mixture of 400 ml of water and 600 ml of ethyl acetate, 2 l of ether and 1 l of low-boiling petroleum ether and dried overnight in vacuo at 45° C. There is obtained white, crystalline, pure title substance of melting point 193°–195° C. (decomposition). The nuclear resonance spectrum and the microanalysis correspond to the given structure.

(c) Preparation of 2-tritylamino-4-selenazolylpyruvic acid ethyl ester 0-[1-(tert.butoxycarbonyl)-1-methylethyl]oxime:

108.2 g of 2-tritylamino-4-selenazolylpyruvic acid ethyl ester (Z)-oxime hydrochloride are dissolved in 400 ml of dimethyl sulphoxide and treated with 400 ml of acetone, 138.3 g of granulated potassium carbonate and 49 g of α-bromoisobutyric acid tert.butyl ester. After stirring for 2 hours at 25° C., a further 70 g of powdered potassium carbonate are added to the mixture. The mixture is stirred for a further 22 hours at 25° C. and while gassing with nitrogen. The resulting, dark suspension is freed from acetone in vacuo at 45° C. and poured into a mixture of 2 l of water and 2 l of ethyl acetate. The aqueous phase is extracted once more with 1 l of ethyl acetate and then discarded. The combined, dark organic phases are washed twice with 1 l of water each time, dried over sodium sulphate and evaporated in vacuo at 40° C. The residual evaporation residue, a brown-black resin, is recrystallized from high-boiling petroleum ether. There is obtained the title substance as beige coloured crystals of melting point > 123° C. From the nuclear resonance spectrum it is evident that the compound is present as a syn/anti mixture (about 70:30). The microanalysis corresponds to the given structure.

(d) Preparation of 2-tritylamino-4-selenazolylpyruvic acid (Z)-0-[1-(tert.butyoxycarbonyl)-1-methylethyl] oxime:

90.5 g of 2-tritylamino-4-selenazolylpyruvic acid ethyl ester 0-[1-(tert.butoxycarbonyl)-1-methylethyl] oxime are heated under reflux conditions in 850 ml of methanol with 140 ml of 2N sodium hydroxide for 1½ hours. The dark solution is evaporated in vacuo at 40° C. The solid evaporation residue is partitioned between 1 l of water and a mixture of 1 l of ethyl acetate and 500 ml of methylene chloride and made acid with 140 ml of 3N aqueous hydrochloric acid. The green organic phase is separated, filtered off from a small amount of separated selenium, washed with water, dried over sodium sulphate and concentrated strongly in vacuo at 40° C. The material which crystallizes out is filtered off under suction, washed with ethyl acetate and low-boiling petroleum ether and dried overnight in vacuo at 45° C. There is obtained pure title substance (pure Z-form) of melting point 167°–168° C. (decomposition). The nuclear resonance spectrum and the microanalysis correspond to the given structure.

(e) Preparation of (6R,7R)-3-(acetoxymethyl)-7-[2-[(-Z)-[1-(tert.butoxycarbonyl)-1-methylethoxy]imino]-[2-2-(tritylamino)-4-selenazolyl]acetamido]-8-oxo-5-thia-1-azabicyclo[4.2.0]oct-2-ene-carboxylic acid tert.butyl ester:

37.1 g of 2-tritylamino-4-selenazolylpyruvic acid (Z)-0-[1-tert.butyoxycarbonyl)-1-methylethyl] oxime are added together with 19.7 g of 7-aminocephalosporanic acid tert.butyl ester to a solution of 5 ml of pyridine in 600 ml of methylene chloride. 13.62 g of dicyclohexylcarbodiimide are added to this solution and the mixture is stirred at 25° C. for 2 hours. The dicyclohexylurea which crystallizes out is filtered off and the yellow filtrate is evaporated in vacuo at 40° C. The evaporation residue is dissolved in 1 l of ethyl acetate. This solution is washed successively with 500 ml of 1N hydrochloric acid, 500 ml of dilute aqueous sodium chloride solution and 500 ml of 5% aqueous sodium hydrogen carbonate solution and evaporated in vacuo at 40° C. An orange-brown foam is obtained as the evaporation residue. For crystallization, this foam is dissolved in 200 ml of ether and a small amount of insoluble material is filtered off. The filtrate is stirred for 30 minutes, the substance crystallizing out partially. After adding 300 ml of isopropyl ether, the mixture is stirred for a further 30 minutes in order to complete the crystallization. The substance is filtered off under suction, washed with isopropyl ether and low-boiling petroleum ether and dried overnight in vacuo at 40° C. There is obtained almost colourless, pure title substance with $[\alpha]_D^{25} = +5°$ (c=2.2 in dimethyl sulphoxide). The nuclear resonance spectrum and the microanalysis correspond to to the given structure.

Example 10

Manufacture of the sodium salt of 1-[[(6R,7R)-7-[(-Z)-2-(2-amino-4-selenazolyl)-2-[(1-carboxy-1-methylethoxy)imino]acetamido]-2-carboxy-8-oxo-5-thia-1-azabicyclo[4.2.0]oct-2-en-3-yl]methyl]pyridinium hydroxide (internal salt):

8.44 g of the disodium salt of (6R,7R)-3-(acetoxymethyl)-7-[(Z)-2-(2-amino-4-selenazolyl)-2-[(1-carboxy-1-methylethoxy)imino]acetamido]-8-oxo-5-thia-1-azabicyclo[4.2.0]oct-2-ene-2-carboxylic acid are added to a solution of 28.48 g of sodium iodide in a mixture of 8.8 ml of water and 8 ml of pyridine at 80° C. The mixture is stirred for 1 hour at 80° C. The dark solution is poured into 400 ml of water and evaporated in vacuo at 45° C. The evaporation residue is dissolved in 450 ml of water and adjusted to pH 1 with 3N aqueous hydrochloric acid. The precipitated decomposition product is filtered off under suction, washed with 100 ml of water and discarded. The light yellow filtrate is washed twice with ethyl acetate and the pH is adjusted to 6 with 3N aqueous sodium hydroxide. Then, it is concentrated strongly in vacuo at 40° C. and finally lyophilized overnight. In order to remove the inorganic salts, the lyophilizate is dissolved in 100 ml of water and added to a column containing 1 kg of Amberlite XAD-2. The organic salts are washed from the column with 3 l of water. Then, the column is eluted with 2 l of water/ethanol (8:2). The fractions containing the substance are concentrated in vacuo at 40° C. and lyophilized overnight. There is obtained pure title substance as a beige, voluminous lyophilizate with $[\alpha]_D^{25} = +3°$ (c=0.8 in water). The nuclear resonance spectrum and the microanalysis correspond to the given structure.

Example 11

Manufacture of the sodium salt of (6R,7R)-3-(acetoxymethyl)-7-[-2-(2-amino-4-selenazolyl)-2-[(Z)-hydroxyimino]-acetamido]-8-oxo-5-thia-1-azabicyclo[4.2.-0]oct-2-ene-2-carboxylic acid:

9.28 g of (6R,7R)-3-[acetoxymethyl)-7-[4-bromo-2-[(Z)-hydroxyimino]acetoacetamido]-8-oxo-5-thia-1-azabicyclo[4.2.0]oct-2-ene-2-carboxylic acid are dissolved in 200 ml of methanol and treated with 2.7 g of selenourea. The mixture is stirred for 1 hour at 25° C. and then 22 ml of a 2N solution of sodium 2-ethylcaproate in ethyl acetate as well as 100 ml of water are added. A small amount of separated selenium is filtered off from the solution. The yellow filtrate is diluted with ethanol to 1000 ml until a slight turbidity occurs and the mixture is stirred for 30 minutes, the sodium salt crystallizing. This salt is filtered off under suction, washed with ethanol and low-boiling petroleum ether and dried overnight in a high vacuum at 40° C. There is obtained pure, yellowish title substance with $[\alpha]_D^{25} = +70.8°$ (c=1 in water). The nuclear resonance spectrum corresponds to the given structure.

Example 12

Manufacture of the sodium salt of (6R,7R)-7-[2-[2-amino-4-selenazolyl]-2-[(Z)-hydroxyimino]-acetamido]-3-methyl-8-oxo-5-thia-1-azabicyclo[4.2.0]oct-2-ene-2-carboxylic acid:

12.2 g of (6R,7R)-7-[4-bromo-2-[(Z)-hydroxyimino]-acetoacetamido]-3-methyl-8-oxo-5-thia-1-azabicyclo[4.2.0]-oct-2-ene-2-carboxylic acid are stirred in 250 ml of ethanol together with 4.06 g of selenourea for 2 hours at 25° C. A small amount of separated selenium is filtered off from the solution. The yellow filtrate is treated with 35 ml of a 2N solution of sodium 2-ethylcaproate in ethyl acetate and the mixture is stirred for 30 minutes. The precipitated sodium salt is filtered off under suction, washed with ethanol and low-boiling petroleum ether and dried overnight in a high vacuum at 40° C. There is obtained pure, beige coloured, amorphous title substance with $[\alpha]_D^{25} = +106°$ (c=1 in water). The nuclear resonance spectrum corresponds to the given structure.

Example 13

Production of dry ampoules for intramuscular administration:

A lyophilizate of 0.5 g of disodium salt of (6R,7R)-7-[2-(2-amino-4-selenazolyl)-2-[(Z)-methoxyimino]--acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid is prepared in the usual manner and filled into an ampoule. Prior to the administration, the lyophilizate is treated with 1.7-2.5 ml of a 1% aqueous lidocaine hydrochloride solution.

Example 14

An interlocking gelatine capsule containing the following ingredients is produced in the usual manner:

| | |
|---|---|
| Methylene (6R,7R)-7-[2-(2-amino-4-selenazolyl)-2-[(Z)-methoxyimino]- acetamido]-3-methyl-8-oxo-5-thia-1-azabicyclo[4.2.0]oct-2-ene-2-carboxylate pivalate | 500 mg |
| Luviskol (water-soluble polyvinylpyrrolidone) | 20 mg |
| Mannitol | 20 mg |
| Talc | 15 mg |
| Magnesium stearate | 2 mg |
| | 557 mg |

What is claimed is:

1. A compound of the formula

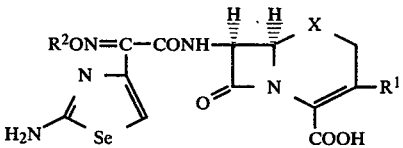

wherein $R^1$ is hydrogen, methyl, methoxy, chlorine, the group —$CH_2Y$ wherein Y is selected from acetoxy, carbamoyloxy, a group of the formula

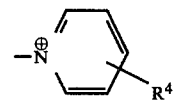

wherein $R^4$ is hydrogen or carbamoyl or the group —$SR^5$ wherein $R^5$ is a 5 or 6 membered heterocyclic ring selected from the group consisting of tetrazolyl, triazolyl, thiadiazolyl or triazinyl being substituted or unsubstituted by lower alkyl, halogen, hydroxy and/or oxo, $R^2$ is hydrogen, lower alkyl or lower alkyl substituted by $COOR^3$, wherein $R^3$ is hydrogen, a cation of a base or a readily hydrolyzable ester selected from lower alkanoyloxyalkyl esters, lower alkoxycarbonyloxyalkyl esters, lactonyl esters, lower alkoxymethyl esters, alkanoylaminomethyl esters, benzyl ester and cyanomethyl esters, and X is sulfur, oxygen or one of the groups —SO— and —$SO_2$— and the readily hydrolyzable esters selected from lower alkanoyloxyalkyl esters, lower alkoxycarbonyloxyalkyl esters, lactonyl esters, lower alkoxymethyl esters, alkanoylaminomethyl esters, benzyl ester and cyanomethyl esters, readily hydrolyzable ethers selected from lower alkanoyloxyalkyl ethers, lower alkoxycarbonyloxyalkyl ethers, lactonyl ethers lower alkoxymethyl ethers and lower alkanoylaminomethyl ethers and salts thereof and hydrates of the compounds of formula I or of their esters, ethers and salts.

2. The compound of claim 1 wherein said compound is in the syn-isomeric form or in the form of mixtures in which the syn-isomeric form predominates.

3. The compound of claim 2, wherein $R^5$ is selected from the 1-methyl-tetrazol-5-yl, 2-methyl-1,3,4-thiadiazol-5-yl, 1,4,5,6-tetrahydro-4-methyl-5,6-dioxo-as-triazin-3-yl, 2,5-dihydro-6-hydroxy-2-methyl-5-oxo-as-triazin-3-yl or 1,2,5,6-tetrahydro-2-methyl-5,6-dioxo-as-triazin-3-yl group.

4. The compound of claim 3, wherein $R^2$ is methyl.

5. The compound of claim 3, wherein $R^2$ is hydrogen.

6. The compound of claim 3, wherein $R^2$ is carboxymethyl.

7. The compound of claim 3, wherein $R^2$ is 1-carboxy-1-methyl-ethyl.

8. The compound of claim 3, wherein $R^2$ is pivaloyloxymethoxycarbonyl-methyl.

9. The compound of claim 8, wherein X is sulfur.

10. The compound: (6R,7R)-7-[2-(2-amino-4-selenazolyl)-2-[(Z)-methoxyimino]-acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid and salts thereof and hydrates of this compound or salts.

11. The compound: (6R,7R)-7-[2-(2-amino-4-selenazolyl)-2-[(Z)-methoxyimino]-acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid 5-oxide and salts thereof and hydrates of this compound or salts.

12. The compound: (6R,7R)-7-[2-(2-amino-4-selenazolyl)-2-[(Z)-methoxyimino]-acetamido]-3-methyl-8-oxo-5-thia-1-azabicyclo-[4.2.0]oct-2-ene-2-carboxylic acid and salts thereof and hydrates of this compound or salts.

13. The compound: (6R,7R)-7-[2-(2-amino-4-selena zolyl-2[(Z)-methoxyimino]-acetamido]-3-[[(5-methyl-1,3,4-thiadiazol-2-yl)thio]methyl]-8-oxo-5-thia-1-azabicyclo[4.2.0]oct-2-ene-2-carboxylic acid and salts thereof and hydrates of this compound or salts.

14. The compound: (6R,7R)-7-[2-(2-amino-4-selenazolyl)-2-[(Z)-methoxyimino]-acetamido]-3-[[(1-methyl-1H-tetrazol-5-yl)thio]methyl]-8-oxo-5-thia-1-azabicyclo[4.2.0]oct-2-ene-2-carboxylic acid and salts thereof and hydrates of this compound or salts.

15. The compound: (6R,7R)-7-[2-(2--amino-4-selenazolyl)-2-[(Z)-methoxyimino]-acetamido]-8-oxo-3-[[(1,4,5,6-tetrahydro-4-methyl-5,6-dioxo-as-triazin-3-yl)thio]methyl]-5-thia-1-azabicyclo[4.2.0]oct-2-ene-2-carboxylic acid and salts thereof and hydrates of this compound or salts.

16. The compound: (6R,7R)-3-(acetoxymethyl)-7-[2-(2-amino-4-selenazolyl)-2-[(Z)-(Z)-methoxyimino]-acetamido]-8-oxo-5-thia-1-azabicyclo[4.2.0]oct-2-ene-2-carboxylic acid and salts thereof and hydrates of this compound or salts.

17. The compound: (6R,7R)-3-(acetoxymethyl)-7[(Z)-2-(2-amino-4-selenazolyl)-2-[(1-carboxy-1-methylethoxy)imino]acetamido]-8-oxo-5-thia-1-azabicyclo[4.2.0]oct-2-ene-2-carboxylic acid and salts thereof and hydrates of this compound or salts.

18. The compound: 1-[[(6R,7R)-7[(Z)-2-(2-amino-4-s-elenazolyl)-2-[(1-carboxy-1-methylethoxy)imino]acetamido]-2-carboxy-8-oxo-5-thia-1-azabicyclo[4.2.0]oct-2-ene-3-yl]methyl]-pyridinium hydroxide (internal salt) and salts thereof and hydrates of this compound or salts.

19. The compound: Methylene (6R,7R)-7-[2-(2-amino-4-selenazolyl)-2-[(Z)-methoxyimino]acetamido]-3-methyl-8-oxo-5-thia-1-azabicyclo[4.2.0]oct-2-ene-2-carboxylate pivalate and the salts thereof and hydrates of this compound or salts.

20. A compound of the formula

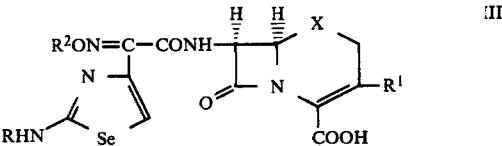

wherein $R^1$ is hydrogen, methyl, methoxy, chlorine, the group —$CH_2Y$ wherein Y is selected from acetoxy, carbamoyloxy, a group of the formula

wherein $R^4$ is hydrogen or carbamoyl or the group —$SR^5$ wherein $R^5$ is a 5 or 6 membered heterocyclic ring selected from the group consisting of tetrazolyl, triazolyl, thiadiazolyl or triazinyl being substituted or unsubstituted by lower alkyl, halogen, hydroxy and/or oxo, $R^2$ is hydrogen, lower alkyl or $COOR^3$-lower alkyl, wherein $R^3$ is hydrogen, a cation of a base or a readily hydrolyzable ester group selected from lower alkanoyloxyalkyl esters, lower alkoxycarbonyloxyalkyl esters, lactonyl esters, lower alkoxymethyl esters, alkanoylaminomethyl esters, benzyl esters and cyanomethyl esters, and X is sulfur, oxygen or one of the groups —SO— and —$SO_2$—, R represents a cleavable protecting group selected from t-butoxycarbonyl, trityl, trifluoroacetyl, chloroacetyl, iodoacetyl or bromoacetyl groups and the carboxy group can be present in protected form.

* * * * *